US008039256B2

(12) United States Patent
Sakai et al.

(10) Patent No.: US 8,039,256 B2
(45) Date of Patent: Oct. 18, 2011

(54) CULTURING METHOD OF MESENCHYMAL STEM CELL

(75) Inventors: Yuhiro Sakai, Itabashi-ku (JP);
Katsuyuki Yamanaka, Itabashi-ku (JP);
Mika Takeda, Hiroshima (JP);
Tomohisa Okura, Hiroshima (JP);
Koichiro Tsuji, Hiroshima (JP)

(73) Assignees: GC Corporation, Tokyo (JP); Two Cells Co., Ltd., Hiroshima-shi (JP)

( * ) Notice: Subject to any disclaimer, the term of this patent is extended or adjusted under 35 U.S.C. 154(b) by 0 days.

(21) Appl. No.: 12/892,223

(22) Filed: Sep. 28, 2010

(65) Prior Publication Data

US 2011/0076770 A1  Mar. 31, 2011

(30) Foreign Application Priority Data

Sep. 28, 2009  (JP) ................................. 2009-222981

(51) Int. Cl.
*C12N 5/00* (2006.01)
*C12N 5/07* (2006.01)
*C12N 5/10* (2006.01)
*C12N 5/071* (2006.01)

(52) U.S. Cl. ........ 435/375; 435/373; 435/325; 435/347; 435/352; 435/363; 435/366; 435/372; 435/377; 435/395

(58) Field of Classification Search .................... 435/375
See application file for complete search history.

(56) References Cited

U.S. PATENT DOCUMENTS

2002/0045260 A1   4/2002   Hung et al.

FOREIGN PATENT DOCUMENTS

| JP | 2004-254519 | 9/2004 |
| WO | WO 01/83709 A1 | 11/2001 |
| WO | WO 02/46501 A2 | 6/2002 |

OTHER PUBLICATIONS

Kaijume et al. Floating culture promotes the maintenance of hematopoietic stem cells. FEBS Letters vol. 581, pp. 4645-4560, 2007.*
Zhang et al. Ceiling culture of mature human adipocytes: use in studies of adipocyte function. Journal of Endocrinology, vol. 164 pp. 119-128, 2000.*
Delle, et al., The Use of Iodixanol for the Purification of Rat Pancreatic Islets. Transplantation Proceedings, vol. 39, pp. 467-469 (2007).*
Optiprep Density Gradient Media product information, Axis-Sheild, Oslo Norway. (2011).*
Graf et al., Enhancement of Hepatic Parenchyma, Aorta, and Portal Vein in Helical CT: Comparison of Iodixanol and Iopromide. American Journal of Roentgenology, vol. 168, pp. 213-217, 1997.*
European Search Report issued Dec. 13, 2010, in European Patent Application No. 10010934.Jul. 2401, filed Sep. 27, 2010 (with English-language Translation).

Daisuke Ishimura, et al. "Differentiation of Adipose-derived Stromal Vascular Fraction Culture Cells into Chondrocytes Using the Method of Cell Sorting with a Mesenchymal Stem Cell Marker" Tohoku J. Exp. Med., 2008, 216, (pp. 149-156).
Wagner, et al. "Comparative Characteristics of mesenchymal stem cells from humn bone marrow, adipose tissue, and umbilical cord blood" Experimental Hematology, Elsevier Inc, US, vol. 33, No. 11, Nov. 1, 2005, (pp. 1402-1416), XP005136979, ISSN: 0301-472X, DOI: DOI: 10.1016/ J. EXPHEM.2005.07.003.
Zvaifler Nathan J, et al. "Mesenchymal precursor cells in the blood of normal individuals" Arthris Research, Current Science, London, GB, vol. 2, on. 6, Aug. 31, 2000, (pp. 477-488), XP021026898, ISSN;1465-9905, DOI: DOI: 10.1186/AR130.
Kasten P, et al. "Instant Stem Cell Therapy: Characterization and Concentration of Human Mesenchymal Stem Cells in Vitro" European Cells and Materials, Swiss Society for Biomate.
Caterson Edward J, et al. "Human marrow-derived mesenchymal progenitor cells: Isolation, culture expansion and analysis of differentiation" Molecular Biotechnology, Humana Press Inc, US, vol. 20, No. 3, Mar. 1, 2002 (pp. 245-256), XP009141649, ISSN: 1073-6085.
Bari De C, et al. "Multipotent mesenchymal stem cells from adult human synovial membrane" Arthritis & Rheumatism. John Wiley & Sons, Inc, US, vol. 44, No. 8, Aug. 1, 2001 (pp. 1928-1942), XP002266867, ISSN: 0004-3591, DOI: DOI: 10.1002/1529-0131 (200108)44.
Zhao P, et al. "Human amniotic mesenchymal cells have some characteristics of cardiomyocytes" Transplantation, Williams and Wilkins, Baltimkore US, vol. 79, No. 5, Mar. 15, 2005 (pp. 528-535), XP003012076, ISSN: 0041- 1337, DOI: DOI: 10.1097/01.TP. 0000149503.92433.39.
Shigematsu M, et al. "Proliferation and Differentiation of Unilocular Fat Cells in the Bone Marrow" Cell Structure and Function, Japan Society for Cell Biology (JSCB), Kyoto, JP, vol. 24, No. 2, Apr. 1, 1999 (pp. 89-100), XP009067456, ISSN: 0386-7196, DOI: DOI: 10.1247/CSF.24.89.
Kuhlmann U, et al. "Production of Doubled Haploid Lines in Frequencies Sufficient for Barley Breeding Programs" Plant Cell Reports, Springer Verlag, DE, vol. 8, No. 2, Jan. 1, 1989 (pp. 78-81), XP009141693, ISSN: 0721-7714.

(Continued)

*Primary Examiner* — Michele K Joike
*Assistant Examiner* — Addison D Ault
(74) *Attorney, Agent, or Firm* — Oblon, Spivak, McClelland, Maier & Neustadt, L.L.P.

(57) ABSTRACT

To efficiently select and proliferate the mesenchymal stem cells without necessity of an exclusive separating device and a complicated separating operation, mesenchymal stem cells are cultured by seeding at least one of a bone marrow solution, an umbilical cord blood, a peripheral blood, a synovial membrane and an amniotic membrane in a liquid culture medium which is filled in a vessel, includes water as its main components and having a specific gravity between 1.06 and 1.10 at 37° C., and making a culture at a temperature 37±2° C. on a ceiling side surface of the vessel, preferably the specific gravity being regulated by use of at least one selected from silica fine powder coated by polyvinyl pyrrolidone, a water soluble copolymer of sucrose and epichlorohydrin, and a water soluble compound including a triiodo aromatic ring.

19 Claims, No Drawings

OTHER PUBLICATIONS

GE healthcare: Instructions Cell preparation media: Ficoll-Plaque Dec. 1, 2008, XP007915955, Retrieved from the Internet: URL:http://www.gelifesciences.com/aptrix/u pp00919.nsf/Content/B667315FF1FF28F4C1257628001D284E/$file/28403956AC.pdf[retrieved on Nov. 24, 2010.

GE Healthcare: Instructions percoll Plus/percoll May 1, 2009, XP007916039, Retrieved from the Internet: URL:http://www.gelifesciences.com/aptrix/u pp00919.nsf/Content/9621EB268A7D5AD1C1257628001D31E9/$file/28903834AB_pdf[retrieved on Nov. 30, 2010.

* cited by examiner

CULTURING METHOD OF MESENCHYMAL STEM CELL

CROSS REFERENCE TO RELATED APPLICATIONS

The present application claims the benefit of the filing date of Japanese Application No. 2009-222981, filed on Sep. 28, 2009.

BACKGROUND OF THE INVENTION

1. Field of the Invention

The present invention relates to a culturing method of mesenchymal stem cells which can select and proliferate the mesenchymal stem cells efficiently without necessity of a specialized separating device and a complicated separating operation.

2. Description of the Conventional Art

Since the mesenchymal stem cells included in a bone marrow solution, an umbilical cord blood, a peripheral blood or the like has a multi-differentiation potency potent capable of differentiating into many kinds of cells such as those of a bone, a cartilage, a fat and the like, attention has been attracted to the mesenchymal cells as a cell source for a cell therapy and a regeneration medical treatment (refer, for example, to International Publication WO01/83709). However, the mesenchymal stem cell has a very low existence frequency, for example, only one per $10^4$ to $10^6$ cells existing in the bone marrow solution of an adult, and in the case of use for a clinical treatment, it is necessary to culture and proliferate the mesenchymal stem cells collected from tissue so as to use them.

In order to use the mesenchymal stem cells as the cell source for the regeneration medical treatment, it is important to secure the mesenchymal stem cells by a method having a high efficiency particularly at a time of a primary culture (a culture until a first replanting is carried out after taking out of a living body), and move to a successive culture (a culture for proliferating and maintaining the cultured cells by removing the cultured cells to a new culture vessel). For example, it is necessary to implant a fixed number or more mesenchymal stem cells for obtaining a good medical treatment result, and it is advantageous if an efficiency of the cell culture from the same amount of a bone marrow solution, an umbilical cord blood, a peripheral blood or the like as their source is high, and the number of the cells obtained by the primary culture is large.

It is well known that in the course of proliferation, senile change of the cells appears uniformly. It has been also known that if the senile change makes progress, a differentiation potency of the cells to a tissue is lowered. If the differentiation potency of the implanted cells is low, a tissue regeneration performance is lowered, and a medical treatment effect is lowered. If the number of the cells obtained at an initial stage is small, additional proliferation is necessary. Accordingly, the senile change makes progress additionally at a time of reaching the fixed number of cells, and a risk is caused.

Further, it has been known that a proliferating capacity is lowered by the senile change. In case that obtained cell number is small, the additional proliferation is necessary. So, the culturing period becomes extremely elongated due to a reduction of the proliferating capacity. In order to establish the medical treatment on the basis of the cell implanting in the future, it is necessary to take a cost thereof into consideration. If the culturing period becomes longer, the cost for the medical treatment becomes higher.

Further, if the efficiency of the primary culture is improved, it is not only possible to reduce an amount of the bone marrow gathered from a patient, to thereby reduce an infestation and a burden applied to the patient, but also possible to freeze and reserve the cells which are surplus after the medical treatment, so as to prepare for a future disease because a lot of cells can be obtained.

The mesenchymal stem cell is a spindle shaped adhesive cell like a fibroblast, and in order to culture the mesenchymal stem cells corresponding to the adhesive cells, it is first of all necessary to adhere to a bottom surface of a plastic dish for culturing. Thereafter, the mesenchymal stem cells are separated from a body fluid by removing non-adhered components such as blood cells or the like mixing in a sample. At this time, since the blood cells such as a red blood cells, a neutrophil, a lymphocyte, a basopil, an eosinophil or the like have larger specific gravities than a specific gravity of the mesenchymal stem cells and settle down earlier, and the number of the blood cells is larger than that of the mesenchymal stem cells in a culture solution, most of the bottom surface of the plastic dish for culturing is covered by those blood cells. As a result, a space for adhering which is necessary for the mesenchymal stem cells is necessarily reduced, and it becomes impossible to obtain a sufficient amount by the primary culture.

Further, in the case that the sample gathered from the living body is constituted by a tissue such as a jaw bone marrow solution, an umbilical cord blood, a peripheral blood or the like, an existence rate of the blood cells or the like is larger in comparison with bone marrow solutions of an iliac bone, a femur or the like. Accordingly, if a seeding amount of the sample is increased for raising a culture density of the mesenchymal stem cells, a density of the blood cells such as the red blood cell or the like becomes higher in proportion thereto, and there is a problem that the adhesion of the mesenchymal stem cells is obstructed.

Then, a method of separating the mesenchymal stem cells from the blood cells such as the red blood cell or the like before culturing has been conventionally carried out. In accordance with this method, it is possible to prepare the mesenchymal stem cells existing in a mononuclear cell fraction at a high purity, however, since aiming at and extracting a fraction having a specific density from a centrifugally separated layer not only require a specialized device and a complicated operation, but also demand a knowledge and a skilled technique, it has been hard to carry out this method commercially. Further, it is necessary to carry out a washing operation again and again for picking up the mesenchymal stem cells from the centrifugally separated layer, the mesenchymal stem cells may be washed away during this process, and it is impossible to efficiently separate the mesenchymal stem cells.

Further, a method of separating and collecting the stem cells by using a filter-shaped stem cell separating device having specific density and fiber diameter is disclosed (refer, for example, to International Publication WO02/46501). This method is a method capable of separating and collecting the stem cells from the bone marrow solution without necessity of addition of a separating reagent and necessity of a centrifugal separating operation. However, since the stem cells are left in the separation material, the method has a great loss and is not efficient.

Further, there exists a separating method of targeting a surface antigen which is characteristic for the mesenchymal stem cell (refer, for example, to Ishimura, D., et al., Differentiation of adipose-derived stromal vascular fraction culture cells into chondrocytes using the method of cell sorting with a mesenchymal stem cell marker. Tohoku J Exp Med, 2008. 216(2): p. 149-56.). It is possible to mark the mesenchymal stem cell corresponding to a target cell by adding a micro bead having such a magnetism as to combine with an antibody against the surface antigen to the sample such as the gathered bone marrow or the like. If the sample is adapted to a separation column put in a magnetic field, the mesenchymal stem cells marked by the magnetism stay in the column, and the other unnecessary cells can be flowed out of the column, whereby it is possible to separate the target cells. The mesenchymal stem cells can be washed out of the column by removing the column from the magnetic field (refer, for example, to Japanese Unexamined Patent Publication No. 2004-254519). Since this method uses the antibody, this is a method capable of more selectively obtaining the mesenchymal stem cells. However, this method has a great loss in the thereafter washing step. Further, there is a risk of an effect by the mesenchymal stem cell joined with the antibody being applied as it is to a clinical treatment and so forth. Further, an exclusive device such as a special antibody, a magnetic bead, a system providing a magnetic field, a column or the like is necessary.

SUMMARY OF THE INVENTION

Problem to be Solved by the Invention

An object of the present invention is to provide a culturing method of mesenchymal stem cells which can solve defects of the prior arts, and can efficiently select and proliferate the mesenchymal stem cells without necessity of an exclusive separating device and a complicated separating operation.

Means for Solving the Problem

The inventors of the present invention have devoted themselves to make a study for solving the problem mentioned above. As a result, they have paid attention to a matter that a specific gravity of the mesenchymal stem cell is lighter than a specific gravity of other blood cells such as a red blood cell or the like, and have found that if the mesenchymal stem cells are cultured in a vessel completely filled with a liquid culture medium including water as its main component and having such a specific gravity that the mesenchymal stem cells float up but adhesion inhibitors such as a red blood cells or the like settle, the mesenchymal stem cells float up so as to be adhered to a ceiling side surface of the vessel and the adhesion inhibitors such as the red blood cell or the like settle down on a bottom surface of the vessel, whereby the mesenchymal stem cells can be adhered to the ceiling side surface of the vessel without their adhesion being obstructed by the adhesion inhibitors such as the red blood cell or the like so as to be capable of culture on the ceiling side surface, and then have completed the present invention.

In other words, in accordance with the present invention, there is provided a culturing method of a mesenchymal stem cell comprising the steps of:

seeding at least one of a bone marrow solution, an umbilical cord blood, a peripheral blood, a synovial membrane and an amniotic membrane in a liquid culture medium which is filled in a vessel, includes water as its main component and having a specific gravity between 1.06 and 1.10 at 37° C.; and making a culture at a temperature 37±2° C. on a ceiling side surface of the vessel, where it is preferable that the specific gravity of the liquid culture medium is regulated by using at least one selected from silica fine powder coated by polyvinyl pyrrolidone, a water soluble copolymer of sucrose and epichlorohydrin, and a water soluble compound including a triiodo aromatic ring.

Effect of the Invention

The culturing method of the mesenchymal stem cell in accordance with the present invention is an excellent culturing method of the mesenchymal stem cell which can be executed simply in a short time without necessity of any complicated separating operation and any exclusive separating apparatus, and depletes a less amount of valuable mesenchymal cells, and displays its greatest capability particularly in a system in which the culture is obstructed by blood cells having a larger specific gravity than the mesenchymal stem cell. A culturing efficiency is improved about several fold to tenfold with regard to the mesenchymal stem cell culture from the bone marrow derived from an iliac bone and a long tube bone. In a clinical study or the like of a regeneration therapy which has been executed in recent years based on implantation of autologous mesenchymal stem cells, the bone marrow of the iliac bone is mainly gathered and the mesenchymal stem cells are cultured therefrom. However, since more mesenchymal stem cells can be obtained on the basis of the culture from the bone marrow by using the culturing method in accordance with the present invention, it is possible to reduce an amount of the bone marrow gathered from the patient. In other words, it is possible to lighten the burden imposed on the patient.

Further, the present invention is useful for culturing the mesenchymal stem cell derived from a bone marrow of a jawbone, an umbilical cord blood and a peripheral blood which are deemed to be hard to be cultured due to reasons that a lot of blood cells coming to adhesion inhibitors are included, an existing amount of the mesenchymal stem cells is small, and so forth. The culture from the bone marrow of the jawbone has a great significance for a dental completed type mesenchymal stem cell medical treatment. Further, the umbilical cord blood which is disposed as a medical waste in many ways can be changed to a so-called gold mine.

DETAILED DESCRIPTION OF PREFERRED EXAMPLE

In the culturing method of the mesenchymal stem cell in accordance with the present invention, the cell to be cultured is an adhesion dependent mesenchymal stem cell. The adhesion dependent cell can be proliferated only after being once attached to an inner surface of the vessel, however, can be efficiently selected and proliferated without being obstructed its adhesion by the blood cells, by executing of the method in accordance with the present invention.

In the present invention, while the method of regulating the specific gravity of the liquid culture medium is not particularly limited, there is for example a method of making a material which is inactive to the mesenchymal stem cell and can regulate such that the specific gravity comes to 1.06 to 1.10 at 37° C. without greatly changing an osmotic pressure thereof, exist in the liquid culture medium including water as its main component. As a specific example of the material which can regulate the specific gravity without changing the osmotic pressure of the mesenchymal stem cell mentioned above, there can be listed up a silica fine powder coated by a polyvinyl pyrrolidone such as percoll (trade name, manufactured by GE Health Care Company), a water soluble copolymer of a sucrose and an epichlorohydrin such as FICOLL (trade name, manufactured by GE Health Care Company), Ficoll Conray and Ficoll Hypaque (both trade names, manufactured by GE Health Care Company), a water soluble compound including a triiodo aromatic ring, and the like.

The method in accordance with the present invention is a method of culturing in a state in which the culture vessel is filled with the liquid culture medium having such a specific gravity that the mesenchymal stem cells float up and the adhesion inhibitors such as the blood corpuscle components or the like such as the red blood corpuscle or the like settle. "The liquid culture medium including water as the main component and having such a specific gravity that the mesenchymal stem cells float up and the adhesion inhibitors such as the blood corpuscle components or the like such as the red blood corpuscle or the like settle specifically requires that the specific gravity is equal to or more than 1.06. The specific gravity is preferably between 1.06 and 1.10, and particularly preferably between 1.070 and 1.095. If the specific gravity is less than 1.06, the mesenchymal stem cells are hard to float up, and are hard to be separated. If it goes beyond 1.10, even the blood corpuscle components such as the red blood corpuscle or the like having a heavy specific gravity float up, and not only it is impossible to adhere only the mesenchymal stem cells to the ceiling side surface of the vessel, but also the cell culture itself is hurt. Accordingly, it can not be used.

In this case, the liquid culture medium can include biological components such as a blood serum and a cell growth factor (cytokine) in order to enhance a cell growth effect by adding chemical components such as sodium, potassium, calcium, magnesium, phosphor, chlorine, an amino acid, a vitamin, a hormone, an antibiotic, an aliphatic acid, a sugar or the like. As the cell growth factor, there can be listed up specifically a platelet derived growth factor (PDGF), a fibroblast growth factor (FGF), an interleukin-6 (IL-6) and the like, and a concentration thereof in use is such a concentration (0.01 to 20 ng/ml) as is used in an ordinary cell culture.

The culture vessel used in the method in accordance with the present invention is not particularly limited as long as it is structured such that the culture can be carried out on the ceiling side surface by being filled with the liquid culture medium, however, a culture flask is optimum. The generally used culture vessel is structured such that a surface treatment is applied to a culture surface to which the cell is normally adhered, whereby the cell is easily adhered. Then, in the method in accordance with the present invention, it is preferable to leave at rest the culture vessel in such a manner that the surface to which the surface treatment is applied comes to the ceiling side. The culture vessel may be left at rest for culturing after separation being previously promoted by applying the culture vessel to a centrifugal machine just after seeding. An incubation temperature may be the same as a normal incubation temperature of a mammalian cell, the temperature between 35 to 39° C. is preferable, and the temperature of 37° C. is more preferable.

After leaving at rest and culturing at the temperature of 37±2° C. until the mesenchymal stem cells are firmly adhered to the culture surface at the ceiling side of the culture vessel (for one day to fourteen days), a first culture medium change is carried out by using a normal culture medium. After the culture medium change, the culture may be carried on in accordance with a normal way by leaving at rest the culture vessel in such a manner that the culture surface (the surface to which the surface treatment is applied) at the ceiling side to which the mesenchymal stem cells are adhered comes to a floor side. The mesenchymal stem cells may be trypsinized and moved to another vessel when the mesenchymal stem cells proliferate to a desired amount, so as to be proliferated in accordance with a normal culture way. After the mesenchymal stem cells are firmly adhered to the culture surface at the ceiling side, a successive culture can be made by the culture solution having the regulated specific gravity while the culture surface being in kept to be at the ceiling side. The mesenchymal stem cells thus cultured can be utilized for a tissue regeneration and augmentation of a bone and a cartilage, a vascularization, an internal organ regeneration, and an implantation to a patient of a graft versus host disease (GVHD) by utilizing an immune tolerance.

EXAMPLES

Next, a description will be given further in detail of the method in accordance with the present invention on the basis of examples, however, the present invention is not limited to these examples Example 1

Mesenchymal Stem Cell Derived from Bone Marrow of Dog Iliac Bone

<Preparation of Bone Marrow Solution>

A bone marrow was gathered by aspirating from five-year-old female HBD dog iliac bone. Having measured a concentration of white blood cells (WBC) and a concentration of red blood cells (RBC) in the gathered bone marrow by using an automatic blood cell counter (trade name: MEK-5150 CELL-TAC, manufactured by Nihon Kohden Corporation), the number of the white blood cells (WBC) in the gathered bone marrow was $12.92 \times 10^4$ cells/µl, and the number of the red blood cells (RBC) was $556 \times 10^4$ cells/µl. The number of the WBC was used as a number of nuclear cells (NC) derived from the bone marrow as a parent population including the mesenchymal stem cells, for seeding at a time of a primary culture. Further, having checked a bone differentiation potency of the cells obtained by the primary culturing method in accordance with the present invention by alizarin red S stain, they stained in red.

<Regulation of Culture Solution>

αMEM culture mediums (all the culture mediums including 1% penicillin streptomycin and 10% cattle fetus blood serum, and being added with 50 µg/ml sodium ascorbate) which were regulated by using Percoll PLUS (trade name, manufactured by GE Health Care Company) such that their specific gravities come to values shown in Table 1 where used for culturing. In this case, a normal αMEM culture medium (the culture medium including 1% penicillin streptomycin and 10% cattle fetus blood serum, and being added with 50 µg/ml sodium ascorbate) which did not include Percoll PLUS was set to a control culture liquid.

<Culturing Procedure>

Procedure 1: The bone marrow having $500 \times 10^4$ cells of the nuclear cells was seeded in a culture flask (trade name: Lab-Tek slide flask, manufactured by Nalgenunc International Company, culture area: 10 cm$^2$) filled with the culture solution regulated as mentioned above, and was left at rest for culturing at a temperature of 37° C., while the surface normally used for culture of the culture flask being set at the ceiling side.

Procedure 2: After leaving at rest and culturing for three days from the start of the culture, the culture medium in the culture flask was removed. The control culture solution was added at 2 ml after the culture flask was inverted (after the ceiling side surface was made to be a lower surface to set the surface normally used for the culture at the floor side), and the culture was carried on for further two days. Thereafter, all the culture solution was removed, and the culture surface was cleaned five times by 10 ml phosphate buffer solution. After sufficient cleaning, the adhered cells to the culture surface were trypsinized by 1 ml trypsin-EDTA, and the number thereof was measured by using a Coulter counter (trade name: Z1S type, manufactured by Beckmann Coulter Company). Results are collectively shown in Table 1.

In this case, a control culture was a case that the control culture solution was used in the procedure 1, and the procedure 2 was applied after leaving at rest and culturing at the temperature of 37° C. while the surface normally used for the culture of the culture flask being set at the floor side.

TABLE 1

|  | example 1-1 | example 1-2 | example 1-3 | Comparative Example 1 | Comparative Example 2 | Comparative Example 3 | Control |
|---|---|---|---|---|---|---|---|
| Specific Gravity of Culture Solution | 1.071 | 1.089 | 1.100 | 1.025 | 1.055 | 1.225 | 1.005 (Control Culture Solution) |
| Culture Surface of Procedure 1 | Ceiling side | Ceiling side | Ceiling side | Ceiling side | Ceiling side | Ceiling side | Floor side |
| Number of Mesenchymal Cells which were adhered and proliferated [cells] | $19.27 \times 10^3$ | $13.45 \times 10^3$ | $10.55 \times 10^3$ | $1.82 \times 10^3$ | $6.51 \times 10^3$ | $4.18 \times 10^3$ | $4.07 \times 10^3$ |

As is apparent from Table 1, in the examples, good cell adhesion can be obtained on the culture surface which is set at the ceiling side. However, with regard to the examples (the comparative examples 1 and 2) in which the specific gravity of the culture solution is less than 1.06, since the cells do not float up, the cells are less adhered to the culture surface at the ceiling side. In the case that the specific gravity is enlarged on the contrary (the comparative example 3), since the adhesion inhibitors seem to simultaneously float up, the adhered cells to the culture surface at the ceiling side are less. All the cells adhered to the ceiling side surface indicate a good proliferating performance.

Further, when the cells obtained by the culturing method in accordance with the present invention were cultured so as to be differentiated into a bone, a cartilage and a fat, the bone differentiation potency was recognized by the alizarin red S stain, the cartilage differentiation potency was recognized by the alcian blue stain, and the fat differential potency was recognized by the oil red-O stain, respectively, and it could be confirmed that the mesenchymal stem cells were securely obtained by the method in accordance with the present invention.

Example 2

Culture of Mesenchymal Stem Cell Derived from Bone Marrow of Dog Jawbone

<Preparation of Bone Marrow Solution>

A bone marrow was gathered by aspirating from five-year-old female HBD dog jawbone under a root furcation of a lower jaw. Having measured a concentration of white blood cells (WBC) and a concentration of red blood cells (RBC) in the gathered bone marrow by using an automatic blood cell counter (trade name: MEK-5150 CELLTAC, manufactured by Nihon Kohden Corporation), the number of the WBC in the gathered bone marrow was $64 \times 10^2$ cells/μl, and the number of the RBC was $423 \times 10^4$ cells/μl. The number of the WBC was used as a number of nuclear cells (NC) derived from the bone marrow as a parent population including the mesenchymal stem cells, for seeding at a time of a primary culture.

<Regulation of Culture Solution>

An αMEM culture medium (including 1% penicillin streptomycin and 10% cattle fetus blood serum, and being added with 50 μg/ml sodium ascorbate) which was regulated to have 1.075 specific gravity by using Percoll PLUS (trade name, manufactured by GE Health Care Company) was used for culturing. In this case, a normal αMEM culture medium (including 1% penicillin streptomycin and 10% cattle fetus blood serum, and being added with 50 μg/ml sodium ascorbate) which did not include Percoll PLUS was set to a control culture liquid.

<Culturing Procedure>

Procedure 1: The bone marrow having $100 \times 10^4$ cells of the nuclear cells was seeded in a culture flask (trade name: Lab-Tek slide flask, manufactured by Nalgenunc International Company, culture area: 10 cm$^2$) filled with about 20 ml of the culture solution regulated as mentioned above, and was left at rest for culturing at a temperature of 37° C. while the culture surface of the culture flask being set at the ceiling side.

Procedure 2: After leaving at rest and culturing for seven days from the start of the culture, the culture medium in the culture flask was removed. The normal culture was carried out by the control culture solution (the culture solution was about 2 ml) after the culture flask was inverted (after the culture surface was set at the floor side). Thereafter, the culture medium was changed three times a week, and the culture was carried on in accordance with a normal method. All the culture solution was removed at a time when the culture surface reached a confluent on the basis of the proliferating of the adhered cells, the adhered cells were trypsinized by means of 0.4 ml trypsin-EDTA, and the successive cultures were carried out. The number of the cells was measured by using the Coulter counter (trade name: Z1S type, manufactured by Beckmann Coulter Company) at each of the successive cultures. As a result, $33.7 \times 10^4$ mesenchymal cells per one culture flask could be obtained at the primary culture, and $4 \times 10^7$ mesenchymal cells per one culture flask could be obtained after three successive cultures.

Comparative Example 4

The bone marrow having $100 \times 10^4$ cells of the nuclear cells was seeded in a culture flask (trade name: Lab-Tek slide flask, manufactured by Nalgenunc International Company, culture area: 10 cm$^2$) filled with about 20 ml of the control culture solution which was not regulated its specific gravity, and was left at rest for culturing at a temperature of 37° C., while the culture surface of the culture flask being set at the ceiling side. However, the well proliferating mesenchymal cells could not be obtained from the control culture.

What is claimed is:

1. A method of culturing mesenchymal stem cells comprising:
    adjusting the specific gravity of aqueous cell culture medium to between 1.06 and 1.10 at 37° C. by addition of at least one substance selected from the group consisting of silica fine powder coated by polyvinyl pyrrolidone, a water soluble copolymer of sucrose and epichlorohydrin, and a water soluble compound comprising a triiodo aromatic ring;
    seeding at least one selected from the group consisting of bone marrow solution, umbilical cord blood, peripheral blood, synovial membrane, and amniotic membrane in a vessel using a sufficient volume of said specific gravity adjusted aqueous cell culture medium such that said vessel is filled;
    and culturing the cells on the ceilin side surface of the vessel at a temperature of 37±2° C.

2. The method of claim 1, wherein the seeding comprises seeding the bone marrow solution.

3. The method of claim 1, wherein the seeding comprises seeding the umbilical cord blood.

4. The method of claim 1, wherein the seeding comprises seeding the peripheral blood.

5. The method of claim 1, wherein the seeding comprises seeding the synovial membrane.

6. The method of claim 1, wherein the seeding comprises seeding the amniotic membrane.

7. The method of claim 1, wherein the specific gravity is between 1.070 and 1.10 at 37° C.

8. The method of claim 1, wherein the specific gravity is between 1.06 and 1.095 at 37° C.

9. The method of claim 1, wherein the specific gravity is between 1.070 and 1.095 at 37° C.

10. The method of claim 1, wherein the at least one substance comprises the silica fine powder coated by polyvinyl pyrrolidone.

11. The method of claim 1, wherein the at least one substance comprises the water soluble copolymer of sucrose and epichlorohydrin.

12. The method of claim 1, wherein the at least one substance comprises the water soluble compound comprising the triiodo aromatic ring.

13. The method of claim 2, wherein the specific gravity is between 1.070 and 1.095 at 37° C.

14. The method of claim 3, wherein the specific gravity is between 1.070 and 1.095 at 37° C.

15. The method of claim 4, wherein the specific gravity is between 1.070 and 1.095 at 37° C.

16. The method of claim 5, wherein the specific gravity is between 1.070 and 1.095 at 37° C.

17. The method of claim 10, wherein the specific gravity is between 1.070 and 1.095 at 37° C.

18. The method of claim 11, wherein the specific gravity is between 1.070 and 1.095 at 37° C.

19. The method of claim 12, wherein the specific gravity is between 1.070 and 1.095 at 37° C.

* * * * *